United States Patent [19]

Cummings

[11] Patent Number: 5,352,674

[45] Date of Patent: * Oct. 4, 1994

[54] CHEMICALLY STABLE GRANULES CONTAINING INSECTICIDAL PHOSPHOROAMIDOTHIOATES

[75] Inventor: Gary Cummings, Moraga, Calif.

[73] Assignee: Valent U.S.A., Walnut Creek, Calif.

[ * ] Notice: The portion of the term of this patent subsequent to Mar. 29, 2011 has been disclaimed.

[21] Appl. No.: 856,485

[22] Filed: Mar. 24, 1992

Related U.S. Application Data

[63] Continuation-in-part of Ser. No. 674,857, Mar. 25, 1991, abandoned.

[51] Int. Cl.$^5$ ............................................. A01N 57/12
[52] U.S. Cl. ................... 514/120; 424/710; 514/642
[58] Field of Search ................. 514/120, 119; 424/710

[56] References Cited

U.S. PATENT DOCUMENTS

| | | | |
|---|---|---|---|
| 378,583 | 2/1888 | Feustell | 424/710 |
| 3,585,022 | 6/1971 | Gray, Jr. et al. | 71/65 |
| 3,622,677 | 11/1971 | Short | 424/361 |
| 3,716,600 | 2/1973 | Magee | 260/959 |
| 3,845,172 | 10/1974 | Magee | 260/956 |
| 3,914,417 | 10/1975 | Magee | 424/219 |
| 3,919,416 | 11/1975 | Cosby | 424/162 |
| 5,075,058 | 12/1991 | Chan et al. | 264/118 |
| 5,100,667 | 3/1992 | Chan et al. | 424/405 |

FOREIGN PATENT DOCUMENTS

| | | |
|---|---|---|
| 0415609 | 3/1991 | European Pat. Off. . |
| 91/11104 | 8/1991 | PCT Int'l Appl. . |

*Primary Examiner*—Richard L. Raymond
*Assistant Examiner*—Brian M. Burn
*Attorney, Agent, or Firm*—Sughrue, Mion, Zinn, Macpeak & Seas

[57] ABSTRACT

Chemically stable granular insecticidal compositions of phosphoroamidothioates and phosphoroamidodithioates are provided. These compositions comprise at least 75 weight percent of ammonium sulfate effective for granulating the insecticidal components. Insecticidal methods employing these granules are also disclosed.

20 Claims, No Drawings

CHEMICALLY STABLE GRANULES CONTAINING INSECTICIDAL PHOSPHOROAMIDOTHIOATES

CROSS-REFERENCE TO RELATED APPLICATIONS

This application is a continuation-in-part of U.S. Ser. No. 07/674,857 filed Mar. 25, 1991 (now abandoned) which is incorporated herein by reference in its entirety.

BACKGROUND OF THE INVENTION

1. Field of the Invention

The present invention is directed to granular compositions containing insecticidal phosphoroamidothioates as well as to methods for employing said compositions. In particular, the present invention is directed to chemically stable granules of insecticidal phosphoroamidothioates which granules contain granular processing aids and a sufficient amount of ammonium sulfate so as to impart chemical stability to the phosphoroamidothioates. The present invention is also directed to methods for killing insects which utilize such compositions.

2. State of the Art

Insecticidal compositions in various forms are available for rather diverse methods of application. The method of preparation of the insecticidal composition is largely determined by the physical and chemical nature of the insecticide and the intended use and method of application of the insecticide to the area to be treated.

Certain phosphoroamidothioates and phosphoroamidodithioates ("phosphoroamidothioates") are known in the art as having excellent insecticidal activity against a variety of insects and in a variety of environments. A particularly important commercial insecticide within these classes of compounds is the insecticide acephate (generic name) or Orthene® (tradename) which can be systemically taken up by a plant so that insects which feed and/or live on the plant are killed, in addition to those insects which directly ingest or are contacted by the insecticide. Acephate and related compounds are described in U.S. Pat. Nos. 3,716,600, 3,845,172 and 3,914,417, which references disclose that in addition to their insecticidal properties, the compounds disclosed therein possess very low mammalian toxicity. Orthene® is commercially produced as a technical grade chemical of about 97 to 99.5% purity.

One method of formulating technical grade phosphoroamidothioates for commercial use is to mix the technical grade powder with an anti-caking agent, such as fumed silica, and a wetting agent. The wetting agent is utilized to wet the insecticide and the anti-caking agent is used to prevent agglomeration of the insecticide in its container. This formulation of insecticide can be applied to crops as a spray solution or as a dust.

Use of phosphoroamidothioates as powders allows for relatively high concentrations of insecticide to be applied to a treatment area, but the powder application suffers from various disadvantages. First, the finely divided particles of active spray may be carried by air currents into areas where harmful effects may occur. In addition, it is difficult to apply sprays or dusts to the soil surface or to lower areas of plants when dense foliage must be penetrated. Finally, powdered phosphoroamidothioates suffer from chemical stability problems due to hydrolytic and catalytic driven degradation which shortens the shelf life of the powdered insecticide.

While the use of granules (e.g., pellets) would overcome some of the inherent difficulties involved in using sprays or dusts, compression formed granular formulations are generally prepared using processing aids such as lubricants, flowability agents, etc. which, in the present invention have been determined to aggravate the chemical stability problems of insecticidal phosphoroamidothioates. In turn, the lack of chemical stability for granular insecticidal phosphoroamidothioates interferes with the commercial feasibility of such formulations.

In the present invention, it has been found that granules of insecticidal phosphoroamidothioates containing processing aids can be made chemically stable by the use of a sufficient amount of ammonium sulfate. Specifically, in the present invention, granules of insecticidal phosphoroamidothioates containing less than about 6 weight percent of processing aids and at least about 75 weight percent of ammonium sulfate possess improved chemical stability as compared to similar granules containing less than 75 weight percent ammonium sulfate. Contrarily, substitution of other commonly employed carrier materials (e.g., bentonite, diatomaceous earth, attapulgite, etc.) for ammonium sulfate in the insecticidal phosphoroamidothioate granules do not impart chemical stability to the granule and, in fact, appear to compound the instability problem.

While the use of minor amounts of ammonium sulfate with phosphoroamidothioates in pellets (granules) is taught in PCT Application No. PCT/US91/11104 (less than 5 weight percent ammonium sulfate); in European Patent Application No. 415,609 (less than 5 weight percent ammonium sulfate); and in U.S. Ser. No. 07/491,497 filed Mar. 16, 1990 and to be issued as U.S. Pat. No. 5,100,667, on Mar. 31, 1992 (less than 40 weight percent ammonium sulfate), the use of at least 75 weight percent ammonium sulfate has not been taught or suggested in these references nor has it been suggested that the use of such amounts would impart improved chemical stability to granules containing insecticidal phosphoroamidothioates as compared to use of less than 75 weight percent.

Likewise, while U.S. Pat. No. 3,585,022, discloses granules containing a pesticide and from 30 to 90 parts by weight of crystalline salt, this reference fails to teach the use of ammonium sulfate or granules of ammonium sulfate in combination with insecticidal phosphoroamidothioates. Moreover, this reference fails to disclose that use of a sufficient amount of ammonium sulfate will impart chemical stability to the phosphoroamidothioates.

SUMMARY OF THE INVENTION

The present invention is directed to the discovery that granules of insecticidal phosphoroamidothioates containing processing aids (less than about 6 weight percent) and a sufficient amount of ammonium sulfate possess superior chemical stability as compared to similar granules containing less ammonium sulfate.

Accordingly, in one of its composition aspects, the present invention is directed to a granular insecticidal composition comprising:

at least about 2 weight percent of an insecticidal compound or mixture of compounds of the formula:

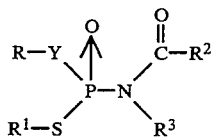

where R and R¹ individually are alkyl, alkenyl or alkynyl containing up to 6 carbons, R² is hydrogen, alkyl containing 1 to 18 carbon atoms, cycloalkyl containing 3 to 8 carbon atoms, alkenyl containing 2 to 18 carbon atoms or alkynyl containing 3 to 18 carbon atoms, R³ is hydrogen or alkyl containing 1 to 6 carbon atoms, and Y is oxygen or sulfur;

at least about 75 weight percent of ammonium sulfate; and one or more processing aids selected from the group consisting of:
(a) from about 0.5 to about 5 weight percent of one or more flowability agents;
(b) from about 0.5 to about 5 weight percent of one or more lubricants;
(c) from about 1 to about 6 weight percent of one or more binders,
with the proviso that the total weight percent of additives (a), (b) and (c) in said granular composition ranges from at least 1 weight percent to less than about 6 weight percent.

In another of its composition aspects, the present invention is directed to a granular insecticidal composition comprising:

from about 2 to about 24 weight percent of an insecticidal compound or mixture of compounds of the formula:

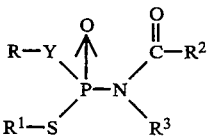

where R and R¹ individually are alkyl, alkenyl or alkynyl containing up to 6 carbons, R² is hydrogen, alkyl containing 1 to 18 carbon atoms, cycloalkyl containing 3 to 8 carbon atoms, alkenyl containing 2 to 18 carbon atoms or alkynyl containing 3 to 18 carbon atoms, R³ is hydrogen or alkyl containing 1 to 6 carbon atoms, and Y is oxygen or sulfur;

about 75 to about 97 weight percent ammonium sulfate; and one or more processing aids selected from the group consisting of:
(a) from about 0.5 to about 5 weight percent of one or more flowability agents;
(b) from about 0.5 to about 5 weight percent of one or more lubricants;
(c) from about 1 to about 6 weight percent of one or more binders,
with the proviso that the total weight percent of additives (a), (b) and (c) in said granular composition ranges from at least 1 weight percent to less than about 6 weight percent.

In one of its method aspects, the present invention is directed to a method for killing insects which comprises contacting insects or their growth habitats with an insecticidally effective amount of granules comprising:

at least about 2 weight percent of a compound of the formula:

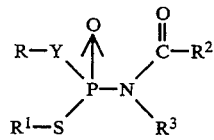

where R and R¹ individually are alkyl, alkenyl or alkynyl containing up to 6 carbons, R² is hydrogen, alkyl containing 1 to 18 carbon atoms, cycloalkyl containing 3 to 8 carbon atoms, alkenyl containing 2 to 18 carbon atoms or alkynyl containing 3 to 18 carbon atoms, R³ is hydrogen or alkyl containing 1 to 6 carbon atoms, and Y is oxygen or sulfur;

at least about 75 weight percent of ammonium sulfate; and one or more processing aids selected from the group consisting of:
(a) from about 0.5 to about 5 weight percent of one or more flowability agents;
(b) from about 0.5 to about 5 weight percent of one or more lubricants;
(c) from about 1 to about 6 weight percent of one or more binders,
with the proviso that the total weight percent of additives (a), (b) and (c) in said granular composition ranges from at least 1 weight percent to less than about 6 weight percent.

In another of its method aspects, the present invention is directed to a method for killing insects which employs the ability of phosphoroamidothioates to be systemically absorbed by plants and when so absorbed, insects ingesting said plants will be killed. This method comprises contacting the root zones of plants which are ingested by said insects or the plant's growth medium with a granular composition comprising:

at least about 2 weight percent of a compound of the formula:

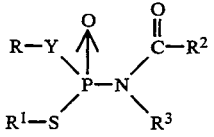

where R and R¹ individually are alkyl, alkenyl or alkynyl containing up to 6 carbons, R² is hydrogen, alkyl containing 1 to 18 carbon atoms, cycloalkyl containing 3 to 8 carbon atoms, alkenyl containing 2 to 18 carbon atoms or alkynyl containing 3 to 18 carbon atoms, R³ is hydrogen or alkyl containing 1 to 6 carbon atoms, and Y is oxygen or sulfur;

at least about 75 weight percent of ammonium sulfate; and one or more processing aids selected from the group consisting of:
(a) from about 0.5 to about 5 weight percent of one or more flowability agents;
(b) from about 0.5 to about 5 weight percent of one or more lubricants;
(c) from about 1 to about 6 weight percent of one or more binders,
with the proviso that the total weight percent of additives (a), (b) and (c) in said granular composition ranges from at least 1 weight percent to less than about 6 weight percent.

DETAILED DESCRIPTION OF THE PREFERRED EMBODIMENTS

The present invention is directed, in part, to the discovery that granular insecticidal compositions of phosphoroamidothioates and related insecticidal compounds which contain specified amounts of granular processing aids possess unexpected and superior chemical stability when these granules contain at least about 75 weight percent ammonium sulfate. Additionally, it has also been unexpectedly discovered that the use of the same level of compounds related to ammonium sulfate or other commonly employed granular carrier materials do not impart similar chemical stability to the granular formulation.

However, prior to defining this invention in further detail, the following terms will first be defined.

1. Definitions

As used herein, the following terms have the definitions given below. If not defined, terms used herein will have their accepted meanings.

As used herein, the term "granules" refer to solid pellets, granules, grains and the like. Such granules can include those wherein the phosphoroamidothioates comprise the core of the granule and the ammonium sulfate forms a coating over the core; those wherein the ammonium sulfate comprises the core of the granule and the phosphoroamidothioates forms a coating over the core; and those wherein there is no discreet core or coatings (i.e., a granule having a substantially uniform composition throughout).

The term "phosphoroamidothioate" refers to a compound or a mixture of compounds of the formula:

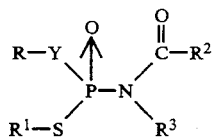

where R and R$^1$ individually are alkyl, alkenyl or alkynyl containing up to 6 carbons, R$^2$ is hydrogen, alkyl containing 1 to 18 carbon atoms, cycloalkyl containing 3 to 8 carbon atoms, alkenyl containing 2 to 18 carbon atoms or alkynyl containing 3 to 18 carbon atoms, R$^3$ is hydrogen or alkyl containing 1 to 6 carbon atoms, and Y is oxygen or sulfur.

Particularly preferred compounds are those in which R and R$^1$ are independently methyl, ethyl, allyl or alkenyl; R$^2$ is H or alkyl; R$^3$ is hydrogen; and Y is oxygen. The most preferred compound is that in which R, R$^1$, and R$^2$ are methyl, R$^3$ is hydrogen and Y is oxygen. Compounds of the above formula may be prepared as described in U.S. Pat. Nos. 3,716,600, 3,845,172 and 3,914,417, which are incorporated herein by reference in their entirety. Likewise, acephate (R, R$^1$, R$^2$ are CH$_3$; R$^3$ is hydrogen and Y is oxygen) is commercially available from Chevron Chemical Company, San Ramon, Calif.[e.g., Orthene® 90S (90% acephate), Orthene® 80S (80% acephate) and Orthene® 75S (75% acephate)].

One or a mixture of the above compounds forms the active insecticidal component in the granular formulation of this invention.

The insecticidal component is generally present in the granule in an amount of from at least 2 weight percent based on the total weight of the granule. Preferably, the insecticidal component will be present in an amount of about 2 to about 24 weight percent based on the total weight of the granule. Even more preferably, the insecticidal component will be present in an amount of about 2 to about 17 weight percent, and still more preferably, the insecticidal component will be present in an amount of from about 5 to about 15 weight percent. Most preferably, the insecticidal component will be present in about 15 weight percent.

The term "granular processing aids" refer to binders, lubricants and flowability aids commonly employed in preparing granules. Binders (binding agents) are often employed in preparing compressed granules in order to increase or maintain the compactness (hardness) of the granule and include by way of example, corn starch, polymers, natural gums, and the like. The specific binder employed is not critical and, when employed, generally from about 0.5 to about 6 weight percent and preferably from about 1 to 6 weight percent of binder is used. However, in those cases where the granules are sufficiently hard without the addition of a binder, the presence of such binders is not necessary.

Lubricants are often employed in granular preparations especially those involving contact with metal or plastic components (e.g., granular preparations made via extrusion) and permit the granule to pass (slide) more readily through or over such components. Suitable lubricants include, by way of example, magnesium stearate, calcium stearate, zinc stearate, silicon emulsions and the like. The particular lubricant employed is not critical and, when employed, generally from about 0.5 to about 5 weight percent and preferably from about 0.2 to about 1 weight percent of lubricant is used based on the total weight of the granule.

Flowability aids ("flow aids") also are often employed in granular preparations and permit the granules to flow more readily during application in the field or from one container to another. Suitable flowability aids include, by way of example, colloidal silica particles, micronized clays or fillers such as bentonite, kaolin, diatomite, attapulgites, and the like. The particular flowability aid employed is not critical and, when employed, generally from about 0.5 to about 5 weight percent and preferably from about 1 to about 5 weight percent of flowability aid is used based on the total weight of the granule.

The present invention is directed, in part, to the discovery that the inclusion of at least one weight percent of one or more of these processing aids has an adverse effect on the chemical stability of insecticidal phosphoroamidothioate granules when prepared in the absence of a sufficient amount of ammonium sulfate (i.e., at least 75 weight percent). The present invention is further directed to the discovery that the inclusion of a sufficient amount of ammonium sulfate in the insecticidal phosphoroamidothioate granules renders the granular composition chemical stable notwithstanding the presence of from at least 1 to less than about 6 weight percent of processing aids.

2. Methodology

The granular formulations of this invention are prepared by admixing the requisite amount of an insecticidal phosphoroamidothioate or a mixture of insecticidal phosphoroamidothioates with at least about 75 weight percent ammonium sulfate (based on the total weight of the granule) in the presence of one or more granular processing aids so as to provide from at least 1 to less than about 6 weight percent of granular processing aids in the final granular composition.

Preferably, the ammonium sulfate will be present in an amount of at least 83 weight percent and even more preferably, in an amount of from about 83 to about 97 weight percent based on the total weight of the granule. In still another preferred embodiment, the ammonium sulfate will be present in an amount of from about 83 to about 92 weight percent and, most preferably, the ammonium sulfate will be present in about 83-85 weight percent.

Preferably, the granular processing aids are employed in amounts ranging from at least 1 weight percent to at least about 5 weight percent and, more preferably, in amounts ranging from at least 1 weight percent to at least about 4 weight percent.

One or more optional additives can be included in this admixture including surfactants and deodorants. Surfactants can be employed to add or retard granule disintegration after application. When employed, the surfactants will generally comprise from about 0.2 to about 5 weight percent of the granular composition.

Deodorants (as well as reodorants) can be used to mask the acephate odor. When employed, the deodorants and reodorants will generally comprise from about 0.05 to about 2 weight percent of the granular composition.

In addition to the above-recited optional ingredients, the granules of this invention can optionally contain one or more active ingredients in combination with the phosphoroamidothioate(s). Such active ingredients include, for example, fungicides, and are employed in amounts effective for their intended purpose (e.g., a fungicidally effective amount).

The complete admixture is then processed into granules. For example, the granules can be made by compression (e.g., compaction) of the complete admixture. Specifically, the complete admixture is generally mixed to uniformity, ground through a hammer mill (e.g., a Fitz hammer mill), compressed (e.g., compacted) at a pressure of at least about 6500 psig (457 kg per square centimeter) and preferably at least 15000 psig (1055 kg per square centimeter), e.g., in a Carver Press or Chilsonator M-83 Compactor, crushed and screened. Other compression methods for preparing granules include, for instance, pelletization, extrusion, briquetting and the like; all of which are well known to the skilled artisan. Preferably, the granules are prepared by compaction.

The granules of this invention are preferably from about 4 mesh to about 60 mesh in size and more preferably from about 16 mesh to about 48 mesh in size.

As set forth above, when used in the concentrations recited herein, the ammonium sulfate imparts chemical stability to the insecticidal phosphoroamidothioate in the granular formulation containing specified amounts of processing aids. As used herein, the term "chemical stability" means that the amount of the insecticidal phosphoroamidothioate in the granular formulation does not diminish by more than about 10% when stored under accelerated storage conditions of 28 days at 50°-55° C. as compared to the amount of the phosphoroamidothioate in the granulation formulation at zero time (e.g., prior to storage). Under these accelerated conditions, insecticidal phosphoroamidothioate granules which do not result in diminished amounts of the phosphoroamidothioate under these accelerated conditions evidence the fact that such granules will possess excellent long term storage stability under ambient conditions. Without being limited to any theory, it is believed that in some way the use of a requisite amount of ammonium sulfate interferes with the degradation of the phosphoroamidothioate thereby imparting chemical stability to the granules.

While the use of ammonium sulfate has been taught in acephate pellets by PCT Appl. No. PCT/US91/11104 (less than 5 weight percent ammonium sulfate); by European Patent Application No. 415,609 (less than 5 weight percent ammonium sulfate); and by U.S. Ser. No. 07/491,497 (to be issued as U.S. Pat. No. 5,100,667 on Mar. 31, 1992) (less than 40 weight percent ammonium sulfate), the amount of ammonium sulfate required to impart chemical stability to phosphoroamidothioate granules is greater than the amount of ammonium sulfate taught in these references. That is to say that the present invention is an improvement over such teachings of ammonium sulfate insofar as when used at the concentrations of this invention, the ammonium sulfate will provide for chemical stability to such granules. Accordingly, this effect is a concentration dependent effect achieved only by using a requisite concentration of ammonium sulfate which concentration is greater than that previously employed.

Once formulated, the granules are useful in a method for controlling insects by application of the granules onto the insecticidal habitat. In general, the granules are applied onto the habitat in an amount effective to be insecticidal to the insects. In a preferred embodiment, the granules are applied at a rate of at least about 0.5 lbs (0.227 kg) acephate per acre and more preferably at a rate of from about 0.5 lbs (0.227 kg) to about 2.0 lbs (0.909 kg) acephate per acre (0.004 square kilometer). Obviously, the amount of granules to be applied per acre (0,004 square kilometer) will depend upon the concentration of acephate in the granules. Thus, for example, granules containing 10% acephate will need to be applied at 5 lbs (2.27 kg) per acre (0.004 square kilometer) to achieve a dosage of 0.5 lbs (0.227 kg) acephate per acre (0.004 square kilometer).

The following examples illustrate certain embodiments of the invention but are not meant to limit the scope of the claims in any way.

EXAMPLES

EXAMPLE 1

The purpose of this example is to demonstrate the criticality of employing less than about 6 weight percent of processing aids with an effective amount of ammonium sulfate in the insecticidal phosphoroamidothioate granule in order to impart chemical stability to the granule.

Five different tests were conducted in order to determine the effect of processing aids on insecticidal phosphoroamidothioate stability in granules.

A. The first test was conducted as follows:

Two different granular formulations containing acephate (Orthene®), ammonium sulfate and either 1 weight percent of processing aids or 6 weight percent of processing aids were prepared and tested under accelerated storage conditions. Specifically, admixtures were prepared as shown in Table 1A below:

TABLE 1A

|  | Weight Percent | |
|---|---|---|
|  | Granule A | Granule B |
| Orthene ® 90-S[1] | 11.1 | 11.1 |
| Cab-O-Sil M-5 | 0.5 | 0.5 |
| Corn Starch | — | 5.0 |
| Magnesium stearate | 0.5 | 0.5 |
| Ammonium Sulfate | 87.9 | 82.9 |

[1] Orthenee ® 90-S contains 90% acephate with the remainder being inerts such as silica and surfactant.

The admixtures were then formulated into granules by first uniformly mixing the admixture. A requisite amount of the mixed admixture was then compacted into round tablets of approximately one square inch (6.45 square centimeters) and ⅛ inch (0.32 cm) thickness. Tablets were then broken by hand and screened to granules of 20 to 50 mesh for use in stability studies.

During compaction, some acephate was lost. Accordingly, the granules were analyzed for the amount of acephate at zero time by gas chromatography. Zero time concentration of acephate can be conducted either by sampling the granules for acephate concentration at the time the granules are prepared, or alternatively, by placing a sample of the granules at the time they are prepared in storage at 0° or less so that the concentration at zero time is preserved. In this latter case, the zero time concentration can be ascertained when the other granular samples are analyzed for acephate concentration. In the examples herein, the zero time concentration was determined by placing the samples in storage at 0° C. or less and then measuring the acephate concentration at the same time other granular samples are removed from accelerated storage conditions.

In any event, the granules are stored in sealed glass bottles maintained at 55° C. (except, of course, for the zero time samples). After storage for 10 and 28 days, the granules were tested for acephate concentration by gas chromatography. The results of these tests are set forth in Table 1B below:

TABLE 1B

| Days in Storage | Amount of Acephate | | | |
|---|---|---|---|---|
|  | Form. A | % Loss | Form. B | % Loss |
| 0 | 10.4 | — | 10.1 | — |
| 10 | 10.5 | — | 7.3 | 28 |
| 28 | 10.5 | — | 7.3 | 28 |

B. The second test was conducted as follows:

Different granular formulations containing acephate (Orthene ®), ammonium sulfate and varying amounts of processing aids were prepared and tested under accelerated storage conditions. Specifically, admixtures were prepared as shown in Table 2A below:

TABLE 2A

|  | Weight Percent in Granules | | | | | | |
|---|---|---|---|---|---|---|---|
|  | C | D | E | F | G | H | I |
| Orthene ® Tech[2] | 15.8 | 15.8 | 15.8 | 15.8 | 15.8 | 15.8 | — |
| Hi-Sil 233 | 3.0 | — | 3.0 | — | — | — | — |
| Hi-Sil 135 | — | 3.0 | — | 3.0 | 6.0 | — | 1.0 |
| Magnesium Stearate | — | — | 0.5 | 0.5 | 0.5 | — | 0.5 |
| Ammonium Sulfate | 81.2 | 81.2 | 80.7 | 80.7 | 77.7 | 84.2 | 81.3 |
| Orthene ® 90-S[1] | — | — | — | — | — | — | 17.2 |

[1] Orthene ® 90-S contains 90% acephate with the remainder being inerts such as silica and surfactant.
[2] Orthene ® Tech contains 97–99% acephate.

The admixtures were then formulated into granules in a manner described above. The granules were stored in sealed glass bottles maintained at 51.7° C. (except for the zero time sample). After storage for 28 days, the granules were tested for acephate concentration by gas chromatography. The results of these tests are set forth in Table 2B below:

TABLE 2B

| Granule | Amount of Initial Acephate Conc. | Amount of Final Acephate Conc. | % Loss |
|---|---|---|---|
| C | 15.1 | 13.9 | 7.9 |
| D | 16.8 | 15.5 | 7.7 |
| E | 16.0 | 14.7 | 8.1 |
| F | 15.8 | 15.5 | 1.9 |
| G | 16.5 | 14.6 | 11.5 |
| H | 15.0 | 15.4 | — |
| I | 15.0 | 14.2 | 5.3 |

The above results demonstrate that when using 6 weight percent or more of processing aids, the resulting granules (formulations B and G) containing phosphoroamidothioates are not chemically stable to phosphoroamidothioate degradation regardless of the fact that an otherwise sufficient amount of ammonium sulfate was employed in the granules whereas when less than 6 weight percent of processing aids are employed, the resulting formulations are stable.

C. The third test was conducted as follows:

A granular formulation containing acephate (Orthene ®), ammonium sulfate and 3.5 weight percent of processing aids was prepared and tested under accelerated storage conditions. Specifically, an admixtures was prepared as set forth in Table 3A below:

TABLE 3A

|  | Weight Percent Formulation J |
|---|---|
| Orthene ® Tech. | 15.3 |
| Hi-Sil 233 | 0.5 |
| Magnesium stearate | 3.0 |
| Ammonium Sulfate | 81.2 |

The admixtures were then formulated into granules in a manner described above. However, some problems were encountered in preparing the samples, and low and high assay materials were blended to obtain a 15.4% assay. The granular materials were stored in sealed glass bottles maintained at 51.7° C. (except for the zero time sample). After storage for 14 days, 28 days and 49 days, the granules were tested for acephate concentration by gas chromatography. The results of these tests are set forth in Table 3B below:

TABLE 3B

| Days in Storage | Amount of Acephate Granule J | | % Loss |
|---|---|---|---|
| 0 | 14.65[3] | (14.5/14.8) | — |
| 14 | 12.75[3] | (12.5/13.0) | 13 |
| 28 | 12.125[3] | (12.25/12.0) | 17.2 |
| 49 | 13.8[4] |  | 5.8 |

[3] = average of two runs
[4] = one run only

The stability value at 28 days for this example is believed to be in error because the value at 49 days is significantly better than that at 28 days and further because there were some problems in preparing the granule.

D. A fourth test was conducted as follows:

Granular formulations containing acephate (Orthene®), ammonium sulfate and varying amounts of processing aids were prepared and tested under accelerated storage conditions. Specifically, admixtures was prepared as set forth in Table 4A below:

TABLE 4A

| | Weight Percent in Granule | | |
|---|---|---|---|
| | K | L | M |
| Orthene ® Tech. | 15.3 | 15.3 | 15.3 |
| Hi-Sil 233 | 3.0 | — | — |
| Hi-Sil 135 | — | 3.0 | 1.5 |
| Magnesium stearate | 0.5 | 0.5 | 0.5 |
| Ammonium Sulfate | 81.2 | 81.2 | 82.7 |

The admixtures were then formulated into granules in a manner described above. The granular materials were stored in either polyethylene rigid container (PE) or an aluminum foil lined bag (Bag) both maintained at 50° C. (except for the zero time sample). After storage for 14 and 28 days, the granules were tested for acephate concentration by gas chromatography. The results of these tests are set forth in Table 4B-I and 4B-II below:

TABLE 4B-I

| Days in Storage | Amount of Acephate in Granule Stored in Bag | | | | | |
|---|---|---|---|---|---|---|
| | K | % Loss | L | % Loss | M | % Loss |
| 0 | 16.2 | — | 15.3 | — | 15.2 | — |
| 14 | 15.2 | 6.2% | 15.3 | — | 15.2 | — |
| 28 | 13.9 | 14.2% | 15.0 | 2% | 13.9 | 8.6% |

TABLE 4B-II

| Days in Storage | Amount of Acephate in Granule Stored in PE | | | | | |
|---|---|---|---|---|---|---|
| | K | % Loss | L | % Loss | M | % Loss |
| 0 | 16.2 | — | 15.3 | — | 15.2 | — |
| 14 | 15.2 | 6.2% | 15.2 | 0.6% | 15.0 | 1.3% |
| 28 | 14.1 | 13% | 15.0 | 2.0% | 13.9 | 8.6% |

With regard to the above data, the inventor has no explanation as to why the stability value for granule K at 28 days is greater than 10% for storage in both the bag and the polyethylene bottle. However, since this data is inconsistent with most of the other data, it is submitted that it is an anomalous result.

E. The fifth test was conducted as follows:

A granular formulation containing acephate (Orthene®), ammonium sulfate and 3.5 weight percent of processing aids was prepared and tested under accelerated storage conditions. Specifically, an admixtures was prepared as set forth in Table 5A below:

TABLE 5A

| | Weight Percent Formulation N |
|---|---|
| Orthene ® Tech. | 16.0 |
| Hi-Sil 233 | 3.0 |
| Magnesium stearate | 0.5 |
| Ammonium Sulfate | 80.5 |

The admixture was then formulated into granules in a manner described above. The granular materials were stored in sealed glass bottles maintained at 51.7° C. (except for the zero concentration).

Three different runs of these granules were prepared and conducted in different glass bottles. Granules from each of these runs were tested for acephate concentration by gas chromatography after storage for 2.1 weeks and 4.1 weeks. Each test was done in duplicate and the results of each of these tests were combined and averaged to provide the composite results set forth in Table 5B below:

TABLE 5B

| Weeks in Storage | Amount of Acephate | |
|---|---|---|
| | Granule N | % Loss |
| 0 | 15.0 | — |
| 2.1 | 14.4[5] | 4% |
| 4.1 | 14.6[6] | 2.7% |

[5] = low of 13.0 in one test and high of 16.0 in one test.
[6] = low of 13.6 in one test and high of 15.1.

The cumulative data presented above demonstrate that the use of at least 75 weight percent of ammonium sulfate provides chemical stability to insecticidal phosphoramidothioate granules containing from at least 1 weight percent to less than 6 weight percent processing aids.

EXAMPLE 2

The purpose of this example is to demonstrate the criticality of employing ammonium sulfate in the insecticidal phosphoroamidothioate granule rather than a related sulfate salt, i.e., potassium sulfate.

Two different granular formulations containing acephate (Orthene®) and either ammonium sulfate or potassium sulfate were prepared and tested under accelerated storage conditions. Specifically, admixtures were prepared as set forth in Table 6A below:

TABLE 6A

| | Weight Percent | |
|---|---|---|
| | Granule A | Granule O |
| Orthene ® 90-S | 11.1 | 11.1 |
| Cab-O-Sil M-5 | 0.5 | 0.5 |
| Magnesium stearate | 0.5 | 0.5 |
| Ammonium Sulfate | 87.9 | — |
| Potassium Sulfate | — | 87.9 |

The admixtures were then formulated into granules by first uniformly mixing the admixture. A requisite amount of the mixed admixture was then compacted into round tablets of approximately one square inch (6.45 square centimeters) and ⅛ inch (0.32 centimeters) thickness. Tablets were then broken by hand and screened to granules of 20 to 50 mesh for use in stability studies.

The granules were stored in sealed glass bottles maintained at 55° C. (except for the zero concentration). After storage for 10 and 28 days, the granules were tested for acephate concentration by gas chromatography. The results of these tests are set forth in Table 6B below:

TABLE 6B

| Days in Storage | Amount of Acephate | | | |
|---|---|---|---|---|
| | Form. A | % Loss | Form. B | % Loss |
| 0 | 10.4 | — | 10.7 | — |
| 10 | 10.5 | — | 9.3 | 13 |
| 28 | 10.5 | — | 9.0 | 16 |

The above results demonstrate that when using a sulfate salt other than ammonium sulfate, granules containing phosphoroamidothioates are not chemically stable to phosphoroamidothioate degradation.

EXAMPLE 3

The purpose of this example is to demonstrate the criticality of employing ammonium sulfate in the insecticidal phosphoroamidothioate granule rather than a related ammonium salt, i.e., ammonium phosphate.

Two different granular formulations containing acephate (Orthene®) and either ammonium sulfate or ammonium phosphate were prepared and tested under accelerated storage conditions. Specifically, admixtures were prepared as set forth in Table 7A below:

TABLE 7A

|  | Weight Percent | |
| --- | --- | --- |
|  | Granule A | Granule P |
| Orthene ® 90-S | 11.1 | 11.1 |
| Cab-O-Sil M-5 | 0.5 | 0.5 |
| Magnesium stearate | 0.5 | 0.5 |
| Ammonium Sulfate | 87.9 | — |
| Ammonium Phosphate | — | 87.9 |

The admixtures were then formulated into granules by first uniformly mixing the admixture. A requisite amount of the mixed admixture was then compacted into round tablets of approximately one square inch and ⅛ inch thickness. Tablets were then broken by hand and screened to granules of 20 to 50 mesh for use in stability studies.

The granules were stored in sealed glass bottles maintained at 55° C. (except for the zero time concentration). After storage for 10 and 28 days, the granules were tested for acephate concentration by gas chromatography. The results of these tests are set forth in Table 7B below:

TABLE 7B

| Days in storage | Amount of Acephate | | | |
| --- | --- | --- | --- | --- |
|  | Granule A | % Loss | Granule P | % Loss |
| 0 | 10.4 | — | 10.4 | — |
| 10 | 10.5 | — | 8.5 | 18 |
| 28 | 10.5 | — | 0 | 100 |

The above results demonstrate that when using an ammonium salt other than ammonium sulfate, granules containing phosphoroamidothioates are not chemically stable to phosphoroamidothioate degradation.

EXAMPLE 4

Insecticidal granules typically can use materials other than ammonium sulfate as the carrier. Such other carrier materials include, for example, bentonite, diatomaceous earth, and attapulgite. The purpose of this example is to demonstrate the criticality of employing ammonium sulfate in the insecticidal phosphoroamidothioate granule rather than substituting other commonly employed granular carrier materials.

Several granular formulations containing acephate (Orthene®), ammonium sulfate, optionally another commonly employed granular carrier materials, and optionally one or more processing aids. Specifically, admixtures were prepared as set forth in Tables 8A-I and 8A-II below:

TABLE 8A-I

|  | Weight Percent of Components in Granules | | | | | |
| --- | --- | --- | --- | --- | --- | --- |
|  | Q | R | S | T | U | V |
| Orthene ® Tech | 26.0 | 26.0 | 26.0 | 26.0 | 21.0 | 21.0 |
| Ammonium Sulfate | 74.0 | 40.0 | 40.0 | 40.0 | 40.0 | 40.0 |
| Hi Sil 135 | — | — | — | 3.0 | — | — |
| Magnesium stearate | — | — | — | 0.5 | — | — |
| Bentonite | — | — | — | — | — | — |
| Diatomaceous Earth | — | — | 34.0 | 30.5 | — | 39.0 |

TABLE 8A-I-continued

|  | Weight Percent of Components in Granules | | | | | |
| --- | --- | --- | --- | --- | --- | --- |
|  | Q | R | S | T | U | V |
| Attapulgite | — | 34.0 | — | — | 39.0 | — |

TABLE 8A-II

|  | Weight Percent of Components in Granules | | | | | |
| --- | --- | --- | --- | --- | --- | --- |
|  | W | X | Y | Z | AA | BB |
| Orthene ® Tech | 26.0 | 16.0 | 16.0 | 5.5 | 21.0 | 21.0 |
| Ammonium Sulfate | 40.0 | 40.0 | 60.0 | 40.0 | 79.0 | 40.0 |
| Hi Sil 135 | — | — | — | — | — | — |
| Magnesium stearate | — | — | — | — | — | — |
| Bentonite | 34.0 | — | — | — | — | 39.0 |
| Diatomaceous Earth | — | — | — | — | — | — |
| Attapulgite | — | 44.0 | 24.0 | 54.5 | — | — |

The admixtures were then formulated into granules in a manner similar to that described in Example 1.

The granules were stored in sealed glass bottles maintained at 50° C. (except for the zero time concentration). After storage for 28 days, the granules were tested for acephate concentration by gas chromatography. The results of these tests are set forth in Tables 8B-I, 8B-II and 8B-III below:

TABLE 8B-I

| Days in Storage | Amount of Acephate in Granule | | | | | | | |
| --- | --- | --- | --- | --- | --- | --- | --- | --- |
|  | Q | % Loss | R | % Loss | S | % Loss | T | % Loss |
| 0 | 25.7 | — | 25.6 | — | 25.4 | — | 25.8 | — |
| 28 | 24.9 | 3.1 | 13.0 | 49.2 | 18.4 | 27.6 | 18.4 | 28.7 |

TABLE 8B-II

| Days in Storage | Amount of Acephate in Granule | | | | | | | |
| --- | --- | --- | --- | --- | --- | --- | --- | --- |
|  | U | % Loss | V | % Loss | W | % Loss | X | % Loss |
| 0 | 20.2 | — | 21.0 | — | 25.6 | — | 15.8 | — |
| 28 | 11.3 | 44.1 | 15.5 | 26.2 | 17.5 | 31.6 | 9.9 | 37.3 |

TABLLE 8B-III

| Days in Storage | Amount of Acephate in Granule | | | | | | | |
| --- | --- | --- | --- | --- | --- | --- | --- | --- |
|  | Y | % Loss | Z | % Loss | AA | % Loss | BB | % Loss |
| 0 | 15.4 | — | 5.4 | — | 20.8 | — | 20.7 | — |
| 28 | 11.5 | 25.3 | 0.7 | 87.0 | 18.8 | 9.6 | 10.0 | 51.7 |

The above data demonstrates that use of only ammonium sulfate with the acephate provides for chemically stable granular compositions and that substituting the ammonium sulfate with substantial amounts of other common granular carriers results in significant instability in the granule.

EXAMPLE 5

The purpose of this example is to demonstrate that the use of minor amounts (e.g., <5 weight percent) of typical granular carriers do not have a significant detrimental effect on the stability of insecticidal phosphoroamidothioate granules containing a significant amount of ammonium sulfate. While the granules of this example are not within the scope of this invention because they do not contain at least 75 weight percent ammonium sulfate and do not possess chemical stability, the side-by-side comparisons of this example are useful for demonstrating the effect on chemical stability for granules containing these components.

Specifically, several granular formulations containing acephate (Orthene®), ammonium sulfate, processing aids and optionally another commonly employed granular carrier materials, were prepared. The admixtures were prepared as set forth in Table 9A below:

TABILE 9A

|  | Weight Percent of Components in Granules | | | |
|---|---|---|---|---|
|  | CC | DD | EE | FF |
| Orthene ® Tech | 26.0 | 26.0 | 26.0 | 26.0 |
| Ammonium Sulfate | 70.5 | 68.0 | 68.5 | 68.5 |
| Hi Sil 135 | 3.0 | 5.5 | 3.0 | 3.0 |
| Magnesium stearate | 0.5 | 0.5 | 0.5 | 0.5 |
| Diatomaceous Earth | — | — | 2.0 | — |
| Attapulgite | — | — | — | 2.0 |

The admixtures were then formulated into granules in a manner similar to that described in Example 1.

The granules were stored in sealed glass bottles maintained at 50° C. (except for the zero time concentration). After storage for 28 days, the granules were tested for acephate concentration by gas chromatography. The results of these tests are set forth in Tables 9B below:

TABLE 9B

| | Amount of Acephate in Granule | | | | | | | |
|---|---|---|---|---|---|---|---|---|
| Days in Storage | CC | % Loss | DD | % Loss | EE | % Loss | FF | % Loss |
| 0 | 25.1 | — | 26.1 | — | 25.7 | — | 25.6 | — |
| 28 | 16.6 | 33.9 | 22.0 | 15.7 | 19.9 | 22.6 | 22.5 | 12.1 |

The above results (Granules CC, EE, and FF) also demonstrate the need to use at least 75 weight percent of ammonium sulfate in order to impart chemical stability.

In view of the fact that the granules of this invention are chemically stable, use of these granules in methods for controlling insects will invariably lead to superior results as compared to granules heretofore used insofar as less amounts of the insecticidal phosphoroamidothioate will diminish over time.

From the foregoing description, various modifications and changes in the composition and method will occur to those skilled in the art. All such modifications coming within the scope of the appended claims are intended to be included therein.

What is claimed is:

1. A granular insecticidal composition comprising:
   at least about 2 weight percent of an insecticidal compound or mixture of compounds of the formula:

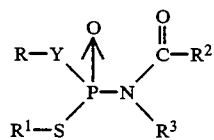

where R and $R^1$ individually are alkyl, alkenyl or alkynyl containing up to 6 carbons, $R^2$ is hydrogen, alkyl containing 1 to 18 carbon atoms, cycloalkyl containing 3 to 8 carbon atoms, alkenyl containing 2 to 18 carbon atoms or alkynyl containing 3 to 18 carbon atoms, $R^3$ is hydrogen or alkyl containing 1 to 6 carbon atoms, and Y is oxygen or sulfur;

at least about 75 weight percent of ammonium sulfate; and
   one or more processing aids selected from the group consisting of:
      (a) from about 0.5 to about 5 weight percent of one or more flowability agents;
      (b) from about 0.5 to about 5 weight percent of one or more lubricants;
      (c) from about 1 to about 6 weight percent of one or more binders,
   with the proviso that the total weight percent of additives (a), (b) and (c) in said granular composition ranges from at least 1 weight percent to less than about 6 weight percent.

2. The composition according to claim 1 wherein R and $R^1$ are independently methyl, ethyl, allyl or alkenyl; $R^2$ is H or alkyl; $R^3$ is hydrogen; and Y is oxygen.

3. The composition according to claim 1 wherein R, $R^1$ and $R^2$ are methyl, $R^3$ is hydrogen and Y is oxygen.

4. A granular insecticidal composition comprising:
   from about 2 to about 24 weight percent of an insecticidal compound or mixture of compounds of the formula:

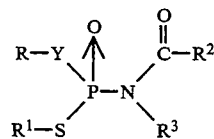

where R and $R^1$ individually are alkyl, alkenyl or alkynyl containing up to 6 carbons, $R^2$ is hydrogen, alkyl containing 1 to 18 carbon atoms, cycloalkyl containing 3 to 8 carbon atoms, alkenyl containing 2 to 18 carbon atoms or alkynyl containing 3 to 18 carbon atoms, $R^3$ is hydrogen or alkyl containing 1 to 6 carbon atoms, and Y is oxygen or sulfur;

from about 75 to about 97 weight percent of ammonium sulfate; and
   one or more processing aids selected from the group consisting of:
      (a) from about 0.5 to about 5 weight percent of one or more flowability agents;
      (b) from about 0.5 to about 5 weight percent of one or more lubricants;
      (c) from about 1 to about 6 weight percent of one or more binders,
   with the proviso that the total weight percent of additives (a), (b) and (c) in said granular composition ranges from at least 1 weight percent to less than about 6 weight percent.

5. The composition according to claim 4 wherein the granular composition comprises at least about 83 weight percent ammonium sulfate.

6. The composition according to claim 5 wherein the granular composition comprises about 15 weight percent of the insecticidal compound or mixture of compounds.

7. The composition according to claim 4 wherein R and $R^1$ are independently methyl, ethyl, allyl or alkenyl; $R^2$ is H or alkyl; $R^3$ is hydrogen; and Y is oxygen.

8. The composition according to claim 4 wherein R, $R^1$ and $R^2$ are methyl, $R^3$ is hydrogen and Y is oxygen.

9. The composition according to claim 1 wherein the granular composition is prepared by compression.

10. A method for killing insects which comprises contacting insects or their growth habitats with an insecticidally effective amount of granules comprising:

at least about 2 weight percent of a compound of the formula:

$$\begin{array}{c} \phantom{R^1-S} O \phantom{\diagup} O \\ R-Y \phantom{a} \diagdown \phantom{a} \diagup C-R^2 \\ \phantom{R^1-}P-N \\ \diagup \phantom{aa} \diagdown \\ R^1-S \phantom{aaaa} R^3 \end{array}$$

where R and $R^1$ individually are alkyl, alkenyl or alkynyl containing up to 6 carbons, $R^2$ is hydrogen, alkyl containing 1 to 18 carbon atoms, cycloalkyl containing 3 to 8 carbon atoms, alkenyl containing 2 to 18 carbon atoms or alkynyl containing 3 to 18 carbon atoms, $R^3$ is hydrogen or alkyl containing 1 to 6 carbon atoms, and Y is oxygen or sulfur;

at least about 75 weight percent of ammonium sulfate; and one or more processing aids selected from the group consisting of:

(a) from about 0.5 to about 5 weight percent of one or more flowability agents;

(b) from about 0.5 to about 5 weight percent of one or more lubricants;

(c) from about 1 to about 6 weight percent of one or more binders, with the proviso that the total weight percent of additives (a), (b) and (c) in said granular composition ranges from at least 1 weight percent to less than about 6 weight percent.

11. The method according to claim 10 wherein said granules comprise at least about 83 weight percent of ammonium sulfate.

12. The method according to claim 10 wherein R and $R^1$ are independently methyl, ethyl, allyl or alkenyl; $R^2$ is H or alkyl; $R^3$ is hydrogen; and Y is oxygen.

13. The method according to claim 12 wherein R, $R^1$ and $R^2$ are methyl, $R^3$ is hydrogen and Y is oxygen.

14. A method for killing insects which comprises contacting insects or their growth habitats with an insecticidally effective amount of granules comprising:

from about 2 to about 24 weight percent of a compound of the formula:

$$\begin{array}{c} \phantom{R^1-S} O \phantom{\diagup} O \\ R-Y \phantom{a} \diagdown \phantom{a} \diagup C-R^2 \\ \phantom{R^1-}P-N \\ \diagup \phantom{aa} \diagdown \\ R^1-S \phantom{aaaa} R^3 \end{array}$$

where R and $R^1$ individually are alkyl, alkenyl or alkynyl containing up to 6 carbons, $R^2$ is hydrogen, alkyl containing 1 to 18 carbon atoms, cycloalkyl containing 3 to 8 carbon atoms, alkenyl containing 2 to 18 carbon atoms or alkynyl containing 3 to 18 carbon atoms, $R^3$ is hydrogen or alkyl containing 1 to 6 carbon atoms, and Y is oxygen or sulfur;

from about 75 to about 97 weight percent of ammonium sulfate; and one or more processing aids selected from the group consisting of:

(a) from about 0.5 to about 5 weight percent of one or more flowability agents;

(b) from about 0.5 to about 5 weight percent of one or more lubricants;

(c) from about 1 to about 6 weight percent of one or more binders, with the proviso that the total weight percent of additives (a), (b) and (c) in said granular composition ranges from at least 1 weight percent to less than about 6 weight percent.

15. The method of claim 14 wherein the granular composition comprises about 15 weight percent of the insecticidal compound.

16. The method of claim 14 wherein R and $R^1$ are independently methyl, ethyl, allyl or alkenyl; $R^2$ is H or alkyl; $R^3$ is hydrogen; and Y is oxygen.

17. The method of claim 14 wherein R, $R^1$ and $R^2$ are methyl, $R^3$ is hydrogen and Y is oxygen.

18. The method of claim 1 wherein the granular composition is prepared by compression.

19. A method for killing insects which comprises contacting the root zones of plants which are ingested by said insects or the plant's growth medium with a granular composition comprising:

at least about 2 weight percent of a compound of the formula:

$$\begin{array}{c} \phantom{R^1-S} O \phantom{\diagup} O \\ R-Y \phantom{a} \diagdown \phantom{a} \diagup C-R^2 \\ \phantom{R^1-}P-N \\ \diagup \phantom{aa} \diagdown \\ R^1-S \phantom{aaaa} R^3 \end{array}$$

where R and $R^1$ individually are alkyl, alkenyl or alkynyl containing up to 6 carbons, $R^2$ is hydrogen, alkyl containing 1 to 18 carbon atoms, cycloalkyl containing 3 to 8 carbon atoms, alkenyl containing 2 to 18 carbon atoms or alkynyl containing 3 to 18 carbon atoms, $R^3$ is hydrogen or alkyl containing 1 to 6 carbon atoms, and Y is oxygen or sulfur;

at least about 75 weight percent of ammonium sulfate; and one or more processing aids selected from the group consisting of:

(a) from about 0.5 to about 5 weight percent of one or more flowability agents;

(b) from about 0.5 to about 5 weight percent of one or more lubricants;

(c) from about 1 to about 6 weight percent of one or more binders, with the proviso that the total weight percent of additives (a), (b) and (c) in said granular composition ranges from at least 1 weight percent to less than about 6 weight percent.

20. A granular insecticidal composition according to claim 1, wherein the composition is prepared by compaction and does not contain any binders.

* * * * *